US 8,214,952 B2
Jul. 10, 2012

(12) United States Patent
Beasley

(10) Patent No.: US 8,214,952 B2
(45) Date of Patent: Jul. 10, 2012

(54) ABDUCTION PILLOW

(76) Inventor: Robert A. Beasley, Cleveland, TN (US)

( * ) Notice: Subject to any disclaimer, the term of this patent is extended or adjusted under 35 U.S.C. 154(b) by 0 days.

(21) Appl. No.: 12/650,063

(22) Filed: Dec. 30, 2009

(65) Prior Publication Data

US 2011/0154571 A1    Jun. 30, 2011

(51) Int. Cl.
*A47C 17/86* (2006.01)
*A47C 20/02* (2006.01)
*A47C 20/04* (2006.01)
*A47C 20/00* (2006.01)

(52) U.S. Cl. .......... 5/648; 5/651; 5/632; 5/630

(58) Field of Classification Search ............. 5/621, 624, 5/630, 632, 648, 650, 651; 297/423.17; 602/23, 602/24
See application file for complete search history.

(56) References Cited

U.S. PATENT DOCUMENTS

| | | | |
|---|---|---|---|
| 4,482,138 A * | 11/1984 | Spann | 5/648 |
| 4,805,605 A | 2/1989 | Glassman | |
| 5,134,739 A * | 8/1992 | Gaffe et al. | 5/648 |
| 5,289,828 A | 3/1994 | Toth | |
| 5,476,105 A | 12/1995 | Toth | |
| 5,871,457 A * | 2/1999 | Swedberg et al. | 602/24 |
| 2009/0229056 A1 | 9/2009 | Edinger | |

* cited by examiner

*Primary Examiner* — Jonathan Liu
(74) *Attorney, Agent, or Firm* — John S. Paniaguas; Katten Muchin Rosenman LLP

(57) ABSTRACT

A hip abduction pillow is used to prevent to post operative hip dislocation of a patient that received a hip prosthesis. The hip abduction pillow in may be integrally formed rigid foam or other suitable material and enables a single person to rotate the patient from side to side with virtually no risk of post operative hip dislocation while minimizing pressure on a patient's heels to virtually eliminate heel pressure sores. The hip abduction pillow includes a base portion; a support portion; and a spacer portion. The hip abduction pillow is self-supporting and can support the patient in two stable alternative rotated positions without the need for a pillow or other support material to maintain a patient in a rotated position.

6 Claims, 5 Drawing Sheets

ABDUCTION PILLOW

BACKGROUND OF THE INVENTION

1. Field of the Invention

The present invention relates to an abduction pillow used which facilitates post operative positioning of the patient while eliminating pressure on a patient's heels as a patient is turned from side to side.

2. Description of the Prior Art

Abduction pillows are well known in the art. Abduction pillows are used to prevent post operative hip dislocation of a patient that received a hip prosthesis. The abduction pillow is used to keep the patient's legs spread apart. As such, hip replacement patients are rolled from one side, for example, 30° from the horizontal, to the other side, 30° from the horizontal in the other direction, to keep weight off the patient's sacrum. The patient is typically rolled from one side to the other every two hours.

A known abduction pillow, a ProCare Model No. 79-901 hip abduction pillow, as manufactured by DJO Incorporated, is illustrated in FIGS. 1-4 and generally identified with the reference numeral 20. The abduction pillow 20 is described and illustrated at http://www.procaresoftgoods.com/index-.asp/fuseaction/products.detail/id/200, hereby incorporated by reference.

Briefly, the abduction pillow 20 is formed in the shape of an isosceles trapezoid having a pair of parallel spaced apart narrow and wide faces 22 and 24, respectively, and a pair of non-parallel equal length faces 26 and 28. As best shown in FIG. 3, the faces 26 and 28 are formed with concave surfaces. These concave surfaces 26 and 28 are configured to receive a patient's legs.

A pair of spaced apart bores 32 and 36 is provided along a longitudinal axis 34 of the abduction pillow 30. The bores 32 and 36 are configured to receive straps 35 and 38 respectively, for securing the abduction pillow 20 to the patient after the patient's legs have been properly positioned in the device.

The abduction pillow 20 is placed between a patient's legs so that the narrow face 22 is placed above a patient's knees and the wide face 24 is placed below the patient's knees so that the patient's feet extend beyond the wide face 24. In order to keep the patient's weight off the sacrum, the patient is rotated from side to side about 30°.

As best shown in FIG. 3, the abduction pillow 20 is formed with a uniform thickness defining generally flat and parallel upper and lower surfaces 40 and 42, respectively. As such, as best shown in FIG. 4, a standard pillow 44 is folded and used to maintain a patient in a rotated position.

There are several problems with the abduction pillow 20. First, as best illustrated in FIG. 4, the weight of both of the patient's legs and the abduction pillow is borne on the patient's heel. This will cause a pressure sore on the outside back of the heel. Secondly, the abduction pillow 20 requires lifting of both of the patient's legs by a nurse which is cumbersome and can result in the nurse getting back pain. Thirdly, two people are required to move the patient from side to side. In particular, one person is required to rotate the patient's legs while a second person is required to fold a pillow and place it in position as shown in FIG. 4.

Other hip abduction pillows are known and described in detail in U.S. Pat. Nos. 4,805,605; 5,289,828; 5,476,105; and US Patent Application Publication No. US 2009/0229056 A1, all hereby incorporated by reference. None of the hip abduction pillows described in these references provide an adequate solution to the problems associated with such hip abduction pillows as set forth below.

U.S. Pat. No. 4,805,605 discloses a hip abduction pillow which includes a base member formed from a bendable material and a spacer. The base member is formed as an isosceles trapezoid with the narrow end placed above the patient's knees and the wide end placed below the patient's knees so that the patient's feet rest on the base member. The spacer is placed above the patient's knees to keep the patient's legs spread apart. In order to ameliorate heel pressure of the patient, the device relies on lowering of the foot end of a standard hospital bed. The device disclosed in the '605 patent relies on placement of the patient and abduction pillow on the hospital bed so that lowering of the foot end of the hospital bed causes bending of the patient's knees which lessens the pressure on a patient's heels. Unfortunately, the abduction pillow disclosed in the '605 patent does not allow a patient to be rotated from side to side.

U.S. Pat. Nos. 5,289,828 and 5,476,105 disclose an abduction pillow that is configured to hold one of the patient's legs in an elevated position and the other leg in a generally flat position. More particularly the abduction pillow disclosed in these patents discloses a wedge shaped device formed as an elevated inclined plane with a central notch for receiving a patient's leg. The lower end of the inclined plane is closest to the patient and the higher end is furthest from the patient. Generally flat bars are disposed on opposing sides of the wedge shaped device. In use, one leg is received in the notch in the wedge shaped device and the other leg is placed along side of the wedge shaped device so that the patient's ankle is resting on one of flat bars. A wedge is placed under the patient's upper torso to maintain the patient in a rotated position. Although the abduction pillow disclosed in these patents ameliorates the problem of heel sores, there are other problems associated with such an abduction pillow. First, rotation of a patient from side to side with such an abduction pillow requires multiple personnel. In particular, one person needs to handle the wedge under the patient's upper torso and one or more persons need to handle the patient's legs. Third, since the patient's legs are not fixed in place during the rotation, rotation of a patient from one side to another can result in post operative dislocation.

US Patent Application No. US 2009/0229056 A1 discloses a hip abduction pillow similar to the hip abduction pillow 20 described above and illustrated in FIGS. 1-4. The main difference is that the hip abduction pillow described in the aforementioned publication is configured with a flexible material to enable a patient to bend their knees.

Thus there is a need for a hip abduction pillow that solves the problems of the prior art that facilitates post operative rotation of a patient after hip replacement surgery while ameliorating heel sores and enables a single person to rotate a patient.

SUMMARY OF THE INVENTION

Briefly, the present invention relates to a hip abduction pillow that is used to prevent postoperative hip dislocation of a patient that received a hip prosthesis. The hip abduction pillow in accordance with the present invention may be integrally formed from a rigid foam or other suitable material and enables a single person to rotate the patient from side to side with virtually no risk of post operative hip dislocation while minimizing pressure on a patient's heels to virtually eliminate heel pressure sores. The hip abduction pillow in accordance with the present invention includes a base portion; a support portion; and a spacer portion. In accordance with one aspect of the invention, the hip abduction pillow in accordance with the present invention is self-supporting and can support the patient in two stable alternative rotated positions without the need for a pillow or other support material to maintain a patient in a rotated position. The base portion may be formed, for example, in the general shape of a triangle defining two support facets. The support facets are configured to be self supported on a flat portion of the patient's bed to provide two stable positions in which the patient's legs are rotated positively or negatively from the plane of the patient's bed. A support portion is formed on top of the base portion defining spaced apart right and left supports. The right and left supports are configured to support the patient's legs and feet. Thus, in use, the patient's heel only supports its own weight. Circular indentations or bores, for example, may be formed in the right and left supports for receiving a patient's heel to further reduce pressure on a patient's heel. The spacer portion is formed between the right and left supports. The spacer portion is formed, for example, in a trapezoid shape, to keep the patient's legs spread apart. Spaced apart bores or notches may be provided in the leg support portion for receiving straps (not shown) for strapping the hip abduction pillow to the patient.

DESCRIPTION OF THE DRAWING

These and other advantages of the present invention will be readily understood with reference to the following specification and attached drawing wherein.

DETAILED DESCRIPTION

The present invention relates to a hip abduction pillow that is used to prevent to post operative hip dislocation of a patient that received a hip prosthesis. The hip abduction pillow may be integrally formed from a rigid foam rubber, for example, medium density polyurethane or other suitable material of comparable stiffness. The hip abduction pillow may alternatively be configured as an inflatable device. Exemplary dimensions for the hip abduction pillow may extend from 2 feet long, 2 feet wide and 15 inches high to 30 inches long, 30 inches wide and 16 inches high.

In accordance with an important aspect of the present invention, the hip abduction pillow enables a single person to rotate the patient from side to side with virtually no risk of post operative hip dislocation while minimizing pressure on a patient's heels to virtually eliminate heel pressure sores. The hip abduction pillow includes a base portion; a leg support portion; and a spacer portion. In accordance with one aspect of the invention, the hip abduction pillow is self-supporting and can support the patient in two stable alternative rotated positions without the need for a pillow or other support material to maintain a patient in a rotated position. The base portion may be formed, for example, in the general shape of a triangle defining two support facets. The support facets are configured to be self supported on a flat portion of the patient's bed to provide two stable positions in which the patient's legs are rotated positively or negatively from the plane of the patient's bed. A support portion is formed on top of the base portion defining spaced apart right and left supports. The right and left supports are configured to support the patient's legs and feet. Thus, in use, the patient's heel only supports its own weight. Circular indentations or bores, for example, may be formed in the right and left supports for receiving a patient's heel to further reduce pressure on a patient's heels. The spacer portion is formed between the right and left supports. The spacer portion is formed, for example, in a trapezoid shape, to keep the patient's legs spread apart. Spaced apart bores or notches may be provided in the support portion for receiving straps (not shown) for strapping the hip abduction pillow to the patient.

Figure 1:
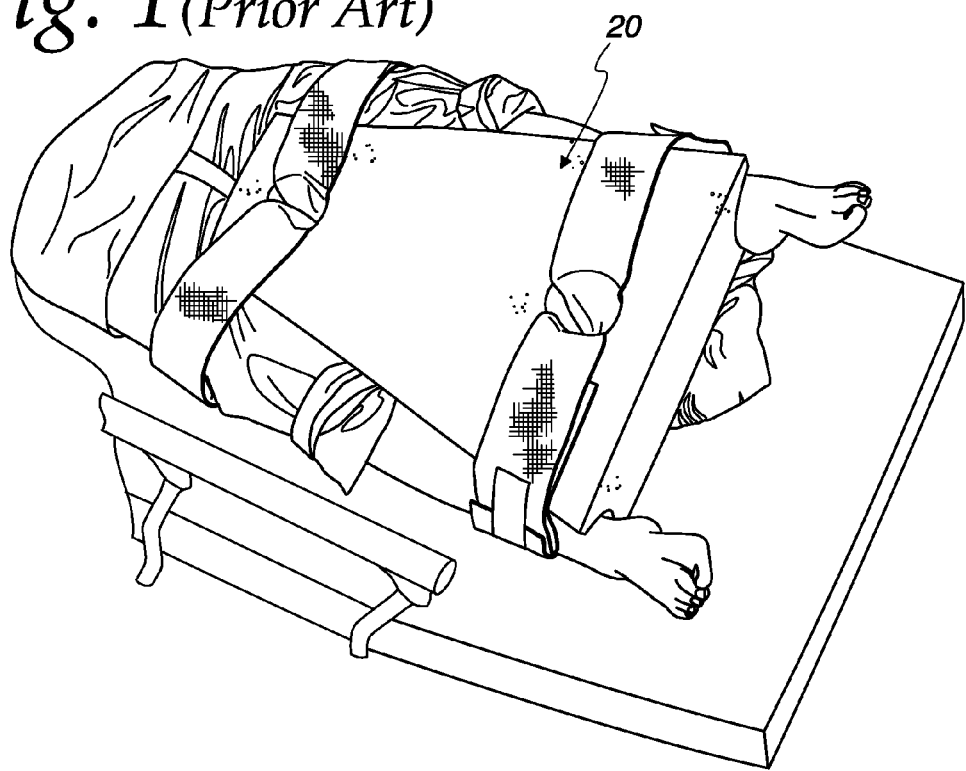
FIG. 1 is an isometric view of patient strapped into a known hip abduction pillow, shown with the patient rotated on their right side and with an upper portion of the patient cut-off.
Figure 2:
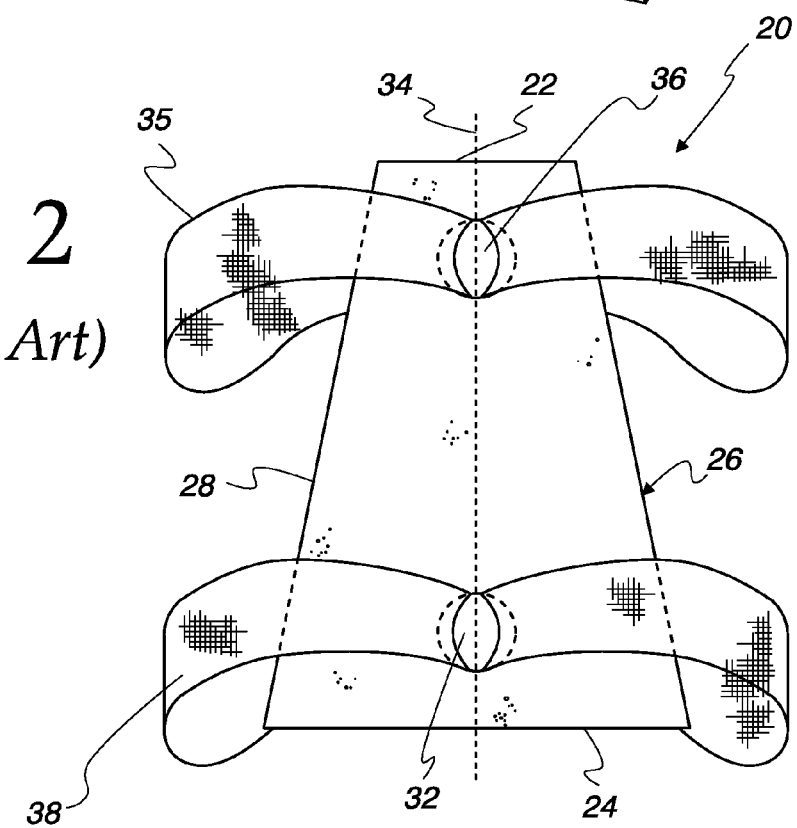
FIG. 2 is a top view of the hip abduction pillow illustrated in FIG. 1.
Figure 3:
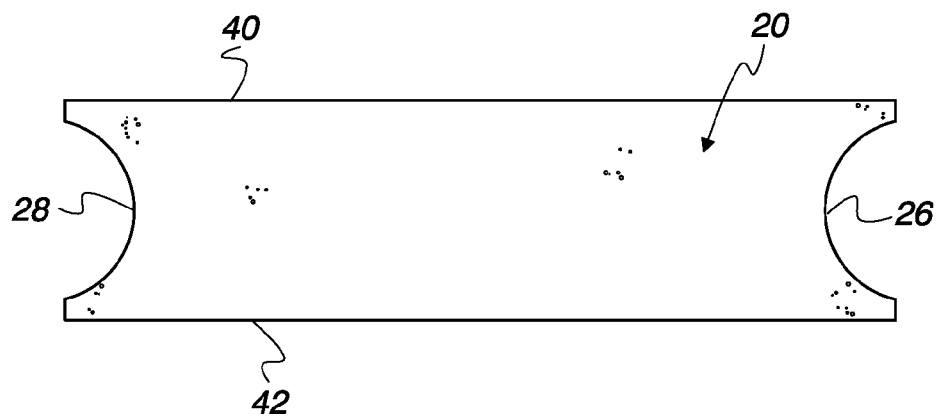
FIG. 3 is a side elevational view of the hip abduction pillow illustrated in FIG. 1.
Figure 4:
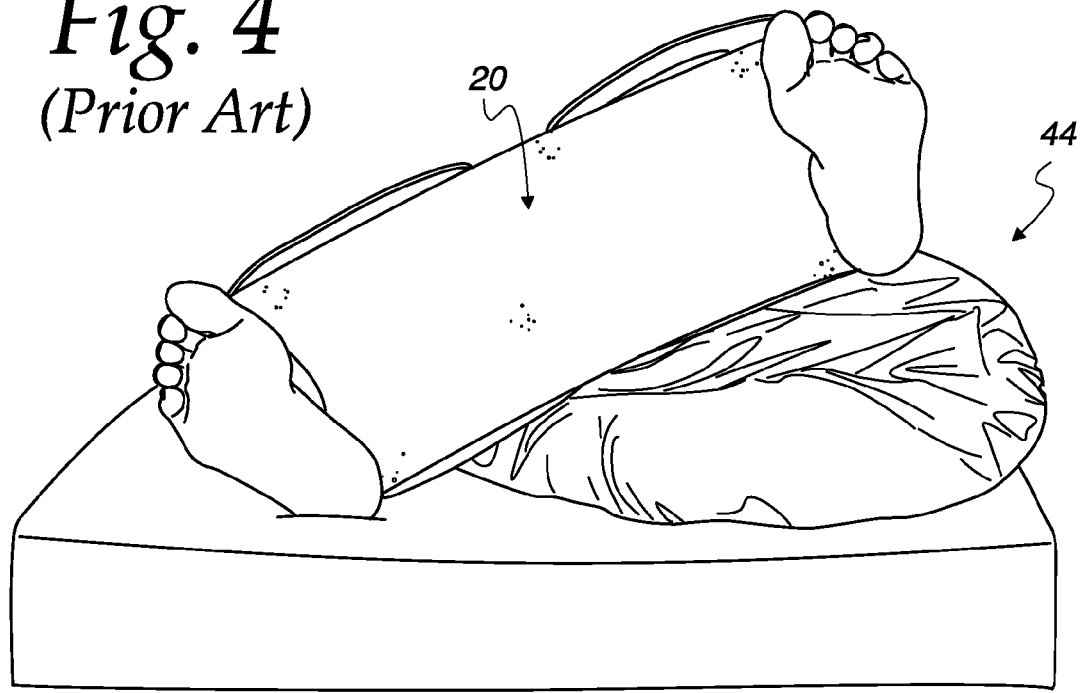
FIG. 4 is an end elevational view illustrating a patient strapped into the hip abduction pillow illustrated in FIG. 1.
Figure 5:
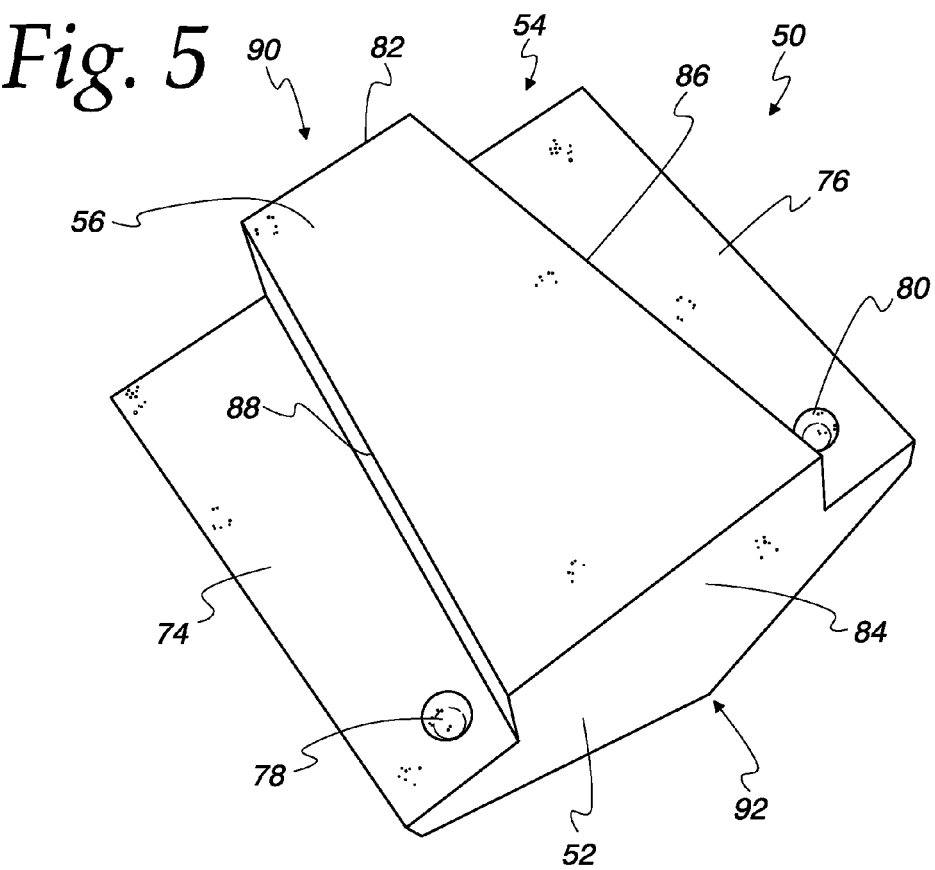
FIG. 5 is an isometric view of the hip abduction pillow in accordance with the present invention.
Figure 6:
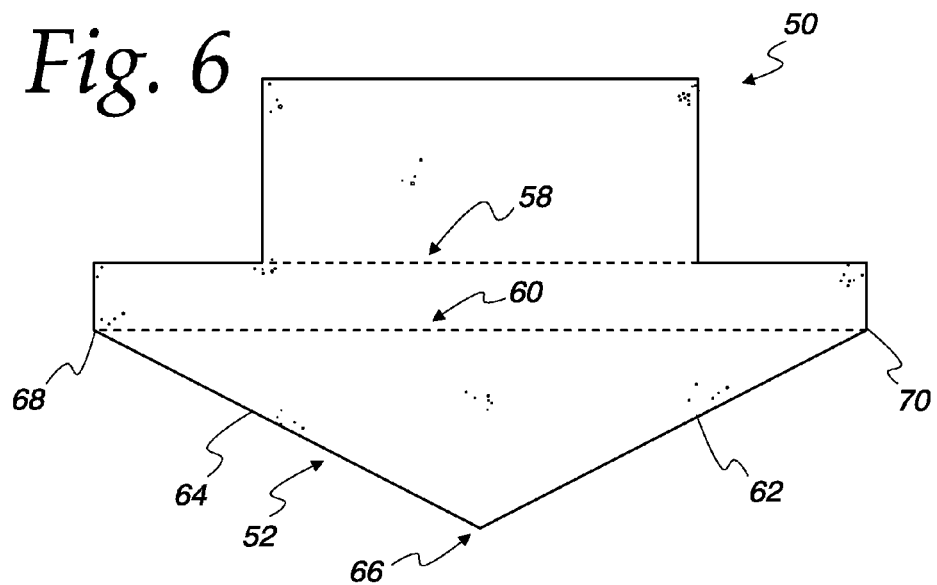
FIG. 6 is an end elevational view of the hip abduction pillow illustrated in FIG. 5
Figure 7:
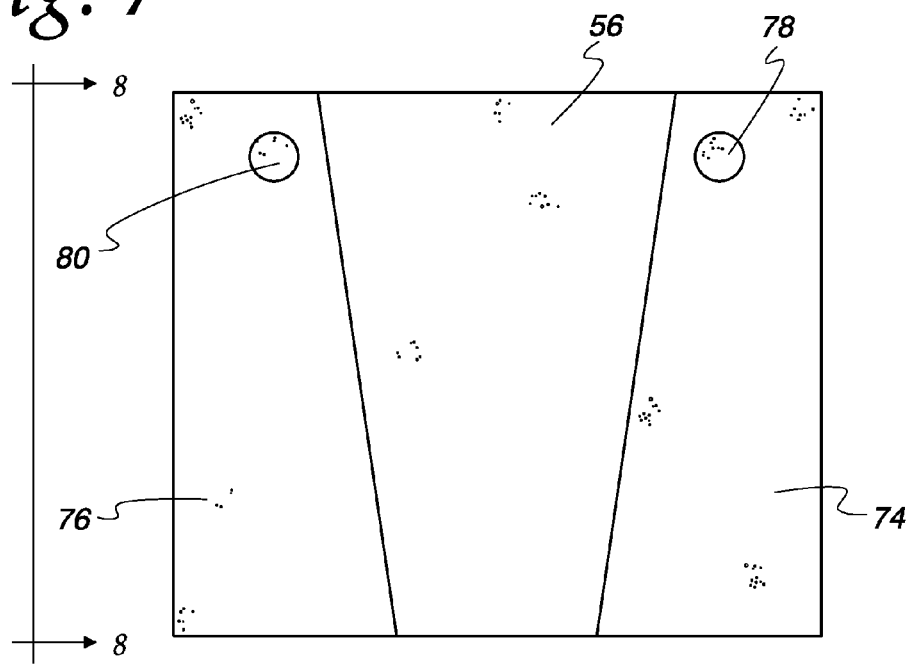
FIG. 7 is a top plan view of the hip abduction pillow illustrated in FIG. 5

The hip abduction pillow in accordance with the present invention is illustrated in FIGS. 5-8 and generally identified with the reference numeral 50. As mentioned above, the hip abduction pillow 50 includes a base portion 52, a support portion, generally identified with the reference numeral 54 and spacer portion 56. In order to describe the hip abduction pillow 50, phantom lines 58 and 60 are illustrated in FIG. 6 to describe the shapes of its constituent parts.

Figure 8:
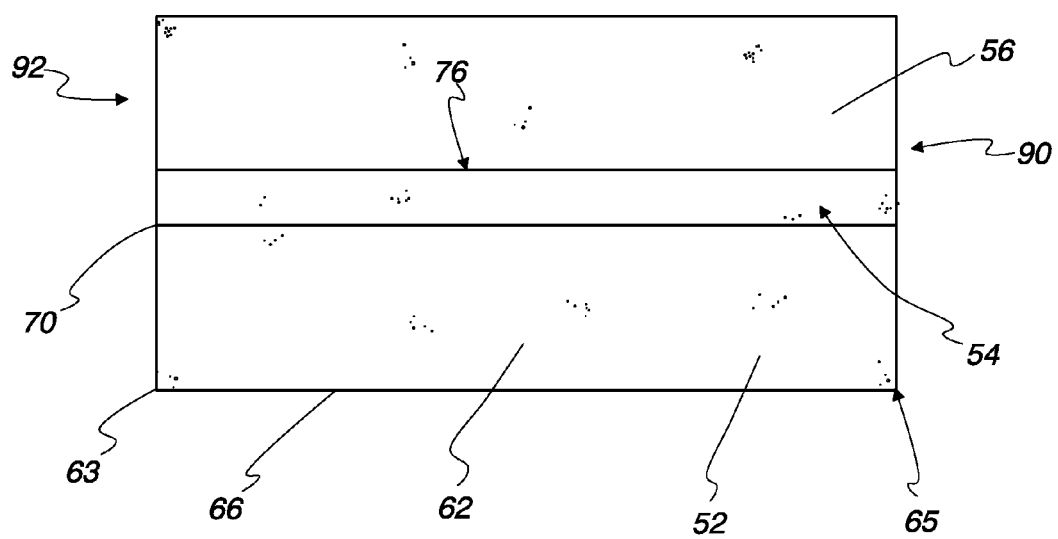
FIG. 8 is a side elevational view of the hip abduction pillow illustrated in FIG. 5

Referring to first to FIG. 6, the base portion 52 is configured with a pair of facets 62 and 64 and an apex portion 66. As shown in FIG. 8, the points 63 and 65 define the apex 66. The apex portion 66 may or may not be parallel to the right and left supports 74 and 76. Each facet 62, 64 (FIG. 6) extends from the apex portion 66 to a support point 68, 70. The apex portion 66 may be as shown or rounded or formed with another shape. The function of the apex portion 66 is to act as a pivot to allow the hip abduction pillow 50 to be rotated while bearing the weight of the patient's legs and the hip abduction pillow and provide support in each of the stable rotated positions.

The facet 64 extends from the apex portion 66 to a right support point 68. Similarly, the facet 62 extends from the apex portion 66 to a left support point 70. The apex portion 66 and the support points 68 and 70 define alternative stable rotated positions of the hip abduction pillow 50. Indeed, with reference to FIG. 6, the hip abduction pillow 50 can be rotated, for example, about 30°, counterclockwise so that the hip abduction pillow 50 is in a first stable position in which the apex portion 66 and the support point 68 are simultaneously in contact with a patient's bed. Similarly, when the hip abduction pillow 50 is rotated clockwise, a second alternative stable position is defined in which the left support point 70 and the apex portion 66 are simultaneously in contact with a patient's bed.

The facets 62 and 64 may be linear extending from the apex portion 66 to the support points 68 and 70. In embodiments in which the facets 62 and 64 are linear, the base portion forms a generally triangular shape. In such embodiments, the facets 62, 64 will alternatively contact the patient's bed in the stable positions and provide support for the patient's legs and the hip abduction pillow in the stable positions. In alternate embodiments, the facets 62, 64 may be formed to be non-linear. For example, the facets 62, 64 may be formed with an arcuate shape in which case, only the apex portion 66 and the support points 68 and 70 provide support in the stable positions.

Referring first to FIG. 5, the support portion 54 may be envisioned as having a generally rectangular shape as illustrated by way of the phantom lines 58 and 60. The support portion 54 is formed above the base portion 52 and defines right and left supports 74 and 76, respectively. The right and left supports 74 and 76 are configured to support a patient's right and left legs and feet, respectively. By supporting a patient's leg and foot on one of the supports 74, 76, a patient's heel will only bear the weight of the patient's foot, thus reducing pressure on the patient's heel. In order to further reduce the pressure on a patient's heel, indentations or bores 78, 80 may optionally be provided, as illustrated in FIG. 5. The indentations 78, 80 may be configured with a circular or other shape to receive a patient's heel so that the weight of the patient's heel is further reduced. The support portion 54 may be configured to extend proximal to a patient's knees and below the patient's feet.

As best shown in FIGS. 5-8, the spacer portion 56 is formed to separate a patient's legs after hip replacement surgery. As shown, the spacer portion 56 is shown with a trapezoid shape. However, other shapes may also be used to space apart a patient's legs. The spacer portion 56 is formed above the base portion 52 between the right and left supports 74 and 76. As shown, the spacer portion 56 may include a pair of generally parallel sides 82 and 84 and a pair non-parallel sides 86 and 88 defining a narrow end 90 and a wide end 92. The spacer portion 56 may be configured to extend proximal to a patient's knees and may be configured to extend distal to a patient's feet.

Figure 9:
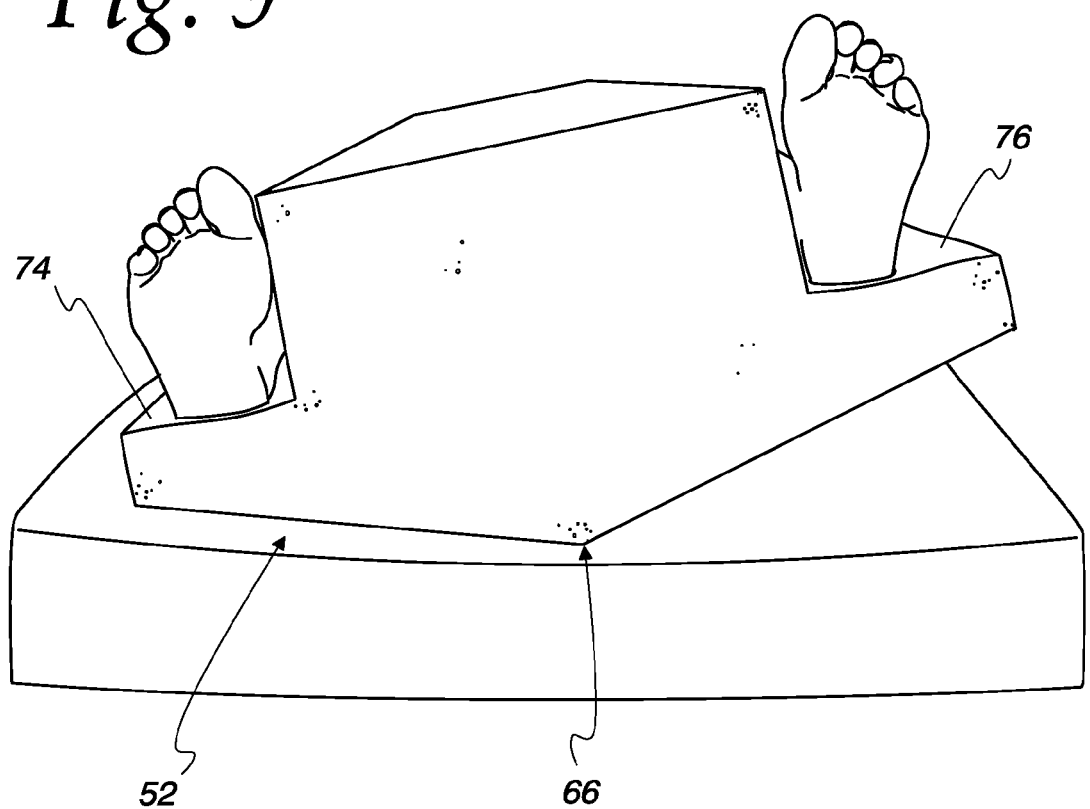
FIG. 9 is an end view illustrating a patient utilizing the hip abduction pillow illustrated in FIG. 5.

As shown best in FIG. 9, the hip abduction pillow 50 in accordance with the present invention is shown in use rotated to one side. In accordance with an important aspect of the invention, the apex portion 66 acts as a pivot point and bears the weight of the patient's legs and feet while the patient is rotated from side to side, thus enabling a person to rotate the patient from side to side with minimal effort. Moreover, the base portion 52 defines stable rotated positions which obviate the need for a regular pillow or other item to support the patient in a rotated position, thus enabling a single person to rotate the patient from side to side. Moreover, in accordance with an important aspect of the invention. The patient's feet are supported by the right and left supports 74 and 76, respectively, thereby reducing the weight on a patient's heel to the weight of the patient's foot or even less if the indentations 78 and 80 are provided.

Obviously, many modifications and variations of the present invention are possible in light of the above teachings. Thus, it is to be understood that, within the scope of the appended claims, the invention may be practiced otherwise than as specifically described above.

I claim:

1. A self-supporting hip abduction pillow formed for rotating a patient from side to side and support a patient in two stable alternative positions, the hip abduction pillow comprising:
    an elongated base portion formed with a triangular cross section defining a centrally located apex that forms a pivot axis and two facets that extend from said apex to support points located on opposing edges of said base portion, said facets being substantially equal in length, said facets also formed to alternatively contact a flat surface defining only two alternative stable positions, wherein said centrally located apex is collinear with a midline of the pillow;
    a support portion formed on top of said base portion, said support portion formed with a rectangular cross section; and
    a spacer portion for maintaining a patient's legs in a spread apart position, said spacer portion formed on top of a portion of said support portion, said spacer portion defining spaced apart right and left supports on said support portion adjacent said spacer portion for supporting the legs of a patient, wherein said apex acts as a pivot to enable the hip abduction pillow to be rotated from one stable position to the other alternative stable position.

2. The hip abduction pillow as recited in claim 1, wherein said spacer portion is generally trapezoidal in shape defining a narrow end and a wide end.

3. The hip abduction pillow as recited in claim 1, wherein said right and left leg supports include indentations adjacent said wide end for receiving a patient's heel.

4. The hip abduction pillow as recited in claim 3, wherein said indentations are generally round.

5. The hip abduction pillow as recited in claim 1, wherein said hip abduction pillow is integrally formed.

6. The hip abduction pillow as recited in claim 1, wherein said hip abduction pillow is formed from rigid foam rubber.

* * * * *